(12) United States Patent
Eisele et al.

(10) Patent No.: US 10,905,824 B2
(45) Date of Patent: Feb. 2, 2021

(54) BOTTLE HOLDER FOR A SYRINGE

(71) Applicant: Henke-Sass, Wolf GmbH, Tuttlingen (DE)

(72) Inventors: Melanie Eisele, Wurmlingen (DE); Fabian Gamboni, Arth (CH)

(73) Assignee: Henke-Sass, Wolf GmbH, Tuttlingen (DE)

( * ) Notice: Subject to any disclaimer, the term of this patent is extended or adjusted under 35 U.S.C. 154(b) by 506 days.

(21) Appl. No.: 15/927,058

(22) Filed: Mar. 20, 2018

(65) Prior Publication Data

US 2018/0272060 A1   Sep. 27, 2018

(30) Foreign Application Priority Data

Mar. 22, 2017   (DE) .......................... 10 2017 106 149

(51) Int. Cl.
| | | |
|---|---|---|
| *A61M 5/162* | (2006.01) | |
| *A61M 5/178* | (2006.01) | |
| *A61J 1/20* | (2006.01) | |
| *A61M 5/14* | (2006.01) | |
| *A61M 5/24* | (2006.01) | |
| *A61M 5/315* | (2006.01) | |

(52) U.S. Cl.
CPC .............. *A61M 5/162* (2013.01); *A61J 1/201* (2015.05); *A61M 5/1417* (2013.01); *A61M 5/1782* (2013.01); *A61J 1/2096* (2013.01); *A61M 5/1418* (2013.01); *A61M 5/31581* (2013.01); *A61M 2005/247* (2013.01); *A61M 2005/2437* (2013.01); *A61M 2005/2477* (2013.01)

(58) Field of Classification Search
CPC .. A61M 5/162; A61M 5/1417; A61M 5/1782; A61M 5/1418; A61M 5/31581; A61M 2005/2437; A61M 2005/247; A61M 2005/2477; A61J 1/201; A61J 1/2096
USPC ........................................................ 604/415
See application file for complete search history.

(56) References Cited

U.S. PATENT DOCUMENTS

| | | | | |
|---|---|---|---|---|
| 4,278,225 A | * | 7/1981 | Phelps ...................... | A61J 1/06 248/311.3 |
| 6,364,866 B1 | * | 4/2002 | Furr .................... | A61M 5/1782 141/330 |

(Continued)

FOREIGN PATENT DOCUMENTS

| | | |
|---|---|---|
| DE | 9409867 U1 | 9/1994 |
| DE | 202010000281 U1 | 7/2011 |

(Continued)

*Primary Examiner* — Andrew J Mensh
(74) *Attorney, Agent, or Firm* — Skaar Ulbrich Macari, P.A.

(57) ABSTRACT

A bottle holder for a syringe includes a stop surface, a piercing hollow spike protruding beyond the stop surface, a guideway, and a first and a second clamping element. Each clamping element includes a through-hole and is moveable back and forth between an insertion position and a clamping position. When the clamping elements are in the insertion position, a neck of the bottle can be moved through the through-holes until the front end of the bottle abuts against the stop surface such that the piercing hollow spike pierces a film at the front end of the bottle. At least one of the clamping elements in its clamping position presses against the neck of the bottle in order to clamp the bottle in the holder.

15 Claims, 6 Drawing Sheets

(56) References Cited

U.S. PATENT DOCUMENTS

| | | | | |
|---|---|---|---|---|
| 6,581,648 B1 * | 6/2003 | Zolentroff | ............ | A61J 1/2096 |
| | | | | 141/2 |
| 2008/0185069 A1 * | 8/2008 | Clark | .................... | A61J 1/2096 |
| | | | | 141/97 |
| 2012/0046635 A1 * | 2/2012 | Hedgepeth | ................ | A61J 1/14 |
| | | | | 604/414 |
| 2015/0247814 A1 * | 9/2015 | Hofmann | ............... | G01N 24/08 |
| | | | | 324/307 |

FOREIGN PATENT DOCUMENTS

| | | | | |
|---|---|---|---|---|
| DE | 102011081797 A1 * | 2/2013 | ............ | A61D 7/00 |
| DE | 102011081797 A1 | 2/2013 | | |
| DE | 202013007396 U1 | 9/2013 | | |

* cited by examiner

BOTTLE HOLDER FOR A SYRINGE

PRIORITY

This application claims the benefit of German Patent Application No. 102017106149.5, filed on Mar. 22, 2017, which is hereby incorporated herein by reference in its entirety.

FIELD

The present invention relates to a bottle holder for a syringe (in particular for a veterinary syringe), wherein the bottle holder comprises a stop surface and a piercing hollow spike protruding beyond the stop surface and extending in a first direction.

BACKGROUND

Syringes are often to be used with bottles of different sizes, so the difficulty arises of holding the bottles securely by means of the bottle holder since bottles of different sizes have different dimensions. Thus, e.g., the diameter of a closing cap arranged on the bottle neck and the height of the closing cap can differ. Therefore, until now, an individual bottle holder or a bottle holder in which at least one part, such as e.g. an adapter piece, is replaceable has been provided for each size of the bottle to be accommodated. This leads to increased effort when changing from a bottle of a first size to a bottle of a second size.

SUMMARY

An object of certain embodiments of the invention is to provide an improved bottle holder.

A bottle holder according to certain embodiments comprises the first and second clamping elements. Thus, at least two different heights of caps of bottles to be accommodated can be held securely and locked in place. At least one of the clamping elements preferably projects into an undercut behind the cap in the region of the neck of the bottle.

The bottle holder according to certain embodiments can comprise a stop surface, a piercing hollow spike protruding beyond the stop surface and extending in a first direction, a guideway and a first and a second clamping element, which are arranged one on another along the first direction and are mounted in the guideway so as to be moveable along a second direction transverse to the first direction. Each of the clamping elements can comprise a through-hole and be moveable back and forth between an insertion position and a clamping position, wherein, when the clamping elements are in the insertion position, a neck of the bottle (including the cap) can be moved through the through-hole until the front end of the bottle abuts against the stop surface with the result that the piercing hollow spike pierces a film at the front end of the bottle, and wherein at least one of the clamping elements, when it is in its clamping position, presses against the neck of the bottle, which abuts with its front end against the stop surface, in order thereby to clamp the bottle in the holder.

As has already been stated, at least one of the clamping elements preferably projects into an undercut behind the cap on the neck of the bottle.

Each clamping element can comprise at least one spring arm which applies a force in the direction towards the clamping position to the clamping element mounted in the guideway. In particular, each clamping element can comprise two spring arms which are preferably arranged in a V shape.

Each clamping element is preferably formed in one piece. For example, the clamping element can be produced from plastic. In particular, the clamping element can be formed as an injection-molded part.

Furthermore, a first and a second stop bar, which extend away from the through-hole, can be provided at the at least one spring arm of each clamping element, wherein the two stop bars define end positions of the movement of the clamping element in the second direction. For this, the guideway can comprise corresponding stop surfaces.

The bottle holder according to certain embodiments can comprise a shell-shaped or basket-shaped holding portion with a wall, wherein the guideway comprises two guideway openings lying opposite each other in the wall. The two openings can be separated from one another by two webs. The webs can provide stop surfaces for the stop bars.

The rim of the through-hole of one of the clamping elements (seen in the first direction onto the clamping element) can comprise two rounded ends of different sizes lying opposite each other along the second direction, which are connected by two connecting sections (for example rectilinear connecting sections). In particular, the shape of the through-hole can be described as oval, egg-shaped or droplet-shaped.

The rounded ends can have any desired curvature shapes or e.g. circular path sections. However, a section of an elliptical path is also possible. The rounded shape can also be approximated e.g. by linear sections.

The end with the larger rounding is preferably designed such that it is larger than the maximum external diameter of a cap of a plurality of medication bottles to be accommodated, which differ in their size. The size of the smaller rounded end is preferably chosen such that it is smaller than the external diameter of the neck of the bottle which has the neck with the smallest external diameter.

In this way it can preferably be guaranteed that, when a bottle is inserted, the clamping element projecting into the undercut bears on it in each case with both connecting sections. A secure fixing can thus be achieved.

The bottle holder can be designed for a set of bottles of different sizes. A system made of bottle holder (optionally together with the syringe) and of the set of bottles is thereby provided.

The through-hole of the clamping elements can be designed e.g. for an external diameter of the cap of from 12 to 35 mm. Furthermore, the clamping elements can be designed for cap heights from 5 to 25 mm and in particular from 5 to 17 mm or 7 to 14 mm.

The through-hole can be completely encircled in at least one of the clamping elements. The clamping element thus comprises an annular clamping section in which the through-hole is formed.

At least one of the clamping elements can be formed such that it is rotationally symmetrical through 180° about an axis along the second direction. It is thus advantageously achieved that an incorrect arrangement of the clamping element in the guideway is prevented.

At least one of the clamping elements can have a constant thickness along the first direction. Furthermore, the clamping elements can lie directly one on another. The clamping elements can all be formed identical. However, it is also possible for clamping elements of different thicknesses to be positioned one on another.

Furthermore, a bottle holder for a syringe is provided, wherein the bottle holder comprises a stop surface, a piercing hollow spike protruding beyond the stop surface and extending in a first direction, a guideway and at least one clamping element, which is mounted in the guideway so as to be moveable along a second direction transverse to the first direction, wherein the at least one clamping element comprises a through-hole and is moveable back and forth between an insertion position and a clamping position. The rim of the through-hole of the at least one clamping element (seen in the first direction onto the clamping element) can comprise two rounded ends of different sizes lying opposite each other along the second direction, which are connected by two connecting sections (preferably rectilinear connecting sections). When the at least one clamping element is in the insertion position, a neck of the bottle can be moved through the through-hole until the front end of the bottle abuts against the stop surface with the result that the piercing hollow spike pierces a film at the front end of the bottle. When the at least one clamping element is in its clamping position, it can press against the neck of the bottle, which abuts with its front end against the stop surface, in order thereby to clamp the bottle in the holder. In particular, in its clamping position, the at least one clamping element can abut against an undercut on the neck of the bottle and thus preferably exert a force on the bottle in the direction towards the stop surface. This bottle holder can be developed in the same way as the bottle holder already described.

Furthermore, a syringe with a bottle holder is provided. The syringe can be a veterinary syringe. In particular, the syringe can be formed as a self-filling syringe.

It is understood that the features mentioned above and those yet to be explained in the following are applicable, not only in the specified combinations, but also in other combinations or singly, without departing from the scope of the present invention.

Figure 1:
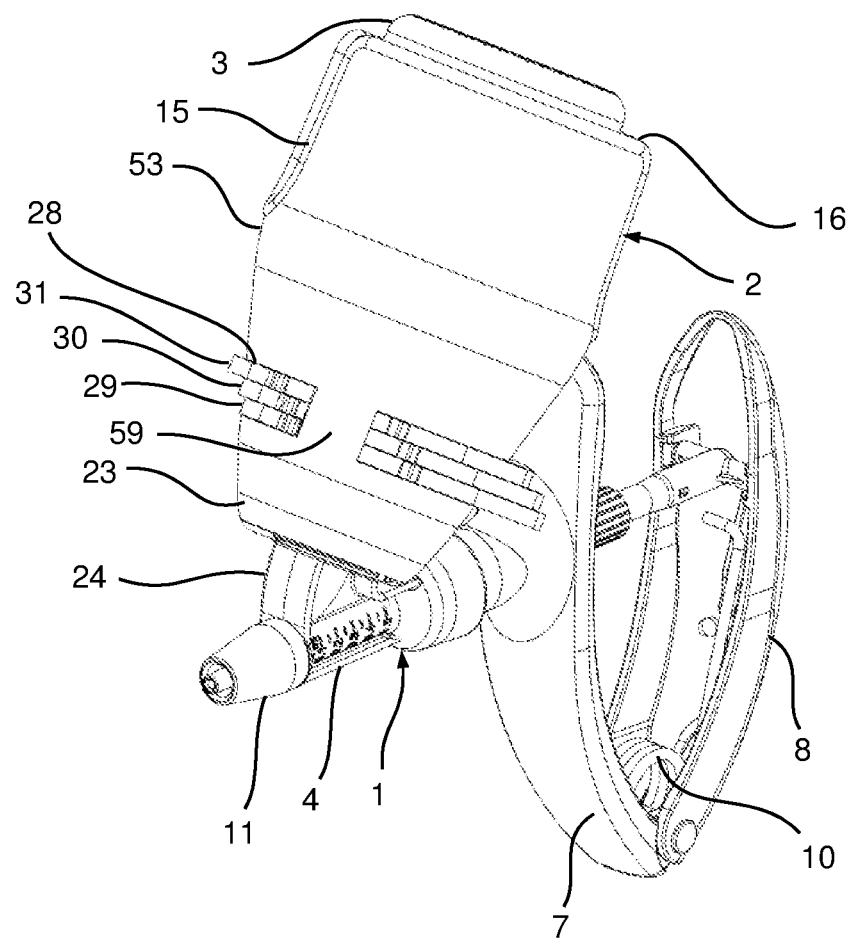
FIG. 1 is a perspective view of a first embodiment of the syringe with a holder in accordance with certain embodiments of the invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

The invention is explained in yet more detail below with the aid of embodiment examples with reference to the attached drawings, which also disclose features essential to the invention. These embodiment examples merely serve the purpose of illustration and are not to be interpreted as limiting. For example, a description of an embodiment example with a plurality of elements or components is not to be interpreted to the effect that all of these elements or components are necessary for the implementation. Rather, other embodiment examples can also contain alternative elements and components, fewer elements or components or additional elements or components. Elements or components of different embodiment examples can be combined with each other, unless otherwise indicated. Modifications and alterations which are described for one of the embodiment examples can also be applicable to other embodiment examples. To avoid repetitions, the same or corresponding elements are given the same reference numbers in different figures and are not explained repeatedly.

In the embodiment shown in FIG. 1, a syringe 1 according to the invention is equipped with a bottle holder 2 according to the invention for a bottle 3, which can in particular be a medication bottle 3.

Figure 3:
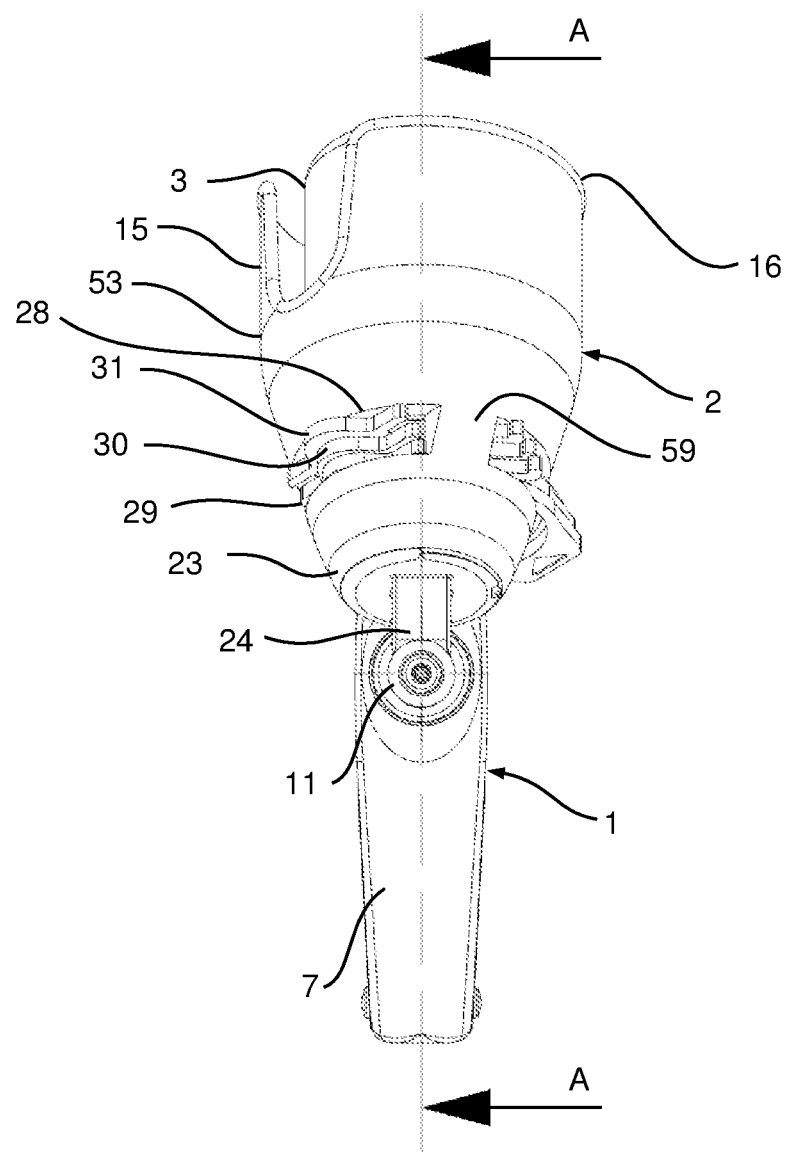
FIG. 3 is a front view of the syringe with holder according to FIG. 1.
Figure 4:
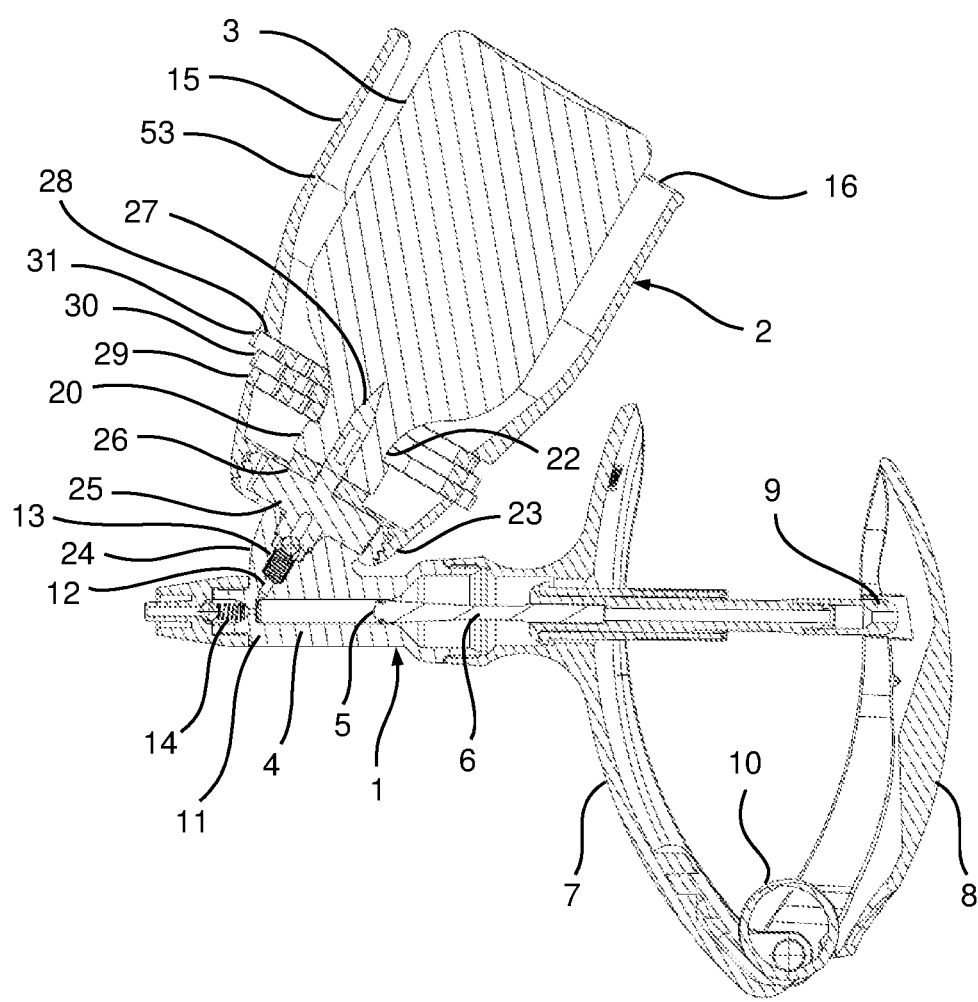
FIG. 4 is a sectional view along the section line A-A from FIG. 3.

The syringe 1 can be formed as a self-filling syringe for veterinary applications, for example, and comprises, as is shown in particular in FIGS. 1, 3 and 4, a syringe cylinder 4, into which a front end 5 of a plunger 6 projects and is displaceable in the longitudinal direction of the syringe cylinder 4. For actuation of the plunger 6, an actuating lever 8, which is connected to a rear end 9 of the plunger 6, is attached pivotably to a handle 7. Arranged between the handle 7 and the operating lever 8 is a spring 10, which holds the actuating lever 8 in the initial position shown in FIG. 4.

When the actuating lever 8 is pivoted from the initial position shown in FIG. 4 towards the handle 7 against the force of the spring, the front end 5 of the plunger 6 is pushed in the syringe cylinder 4 towards the front end 11 of the syringe 1 with the result that a fluid located in the syringe cylinder 4 or a liquid located in the syringe cylinder 4 (the fluid or the liquid can be a medication) is dispensed via the front end 11.

When force is no longer exerted on the actuating lever 8, the latter is pivoted back into the initial position shown in FIG. 4 as a result of the spring 10. In the case of this movement of the plunger 6 from left to right, seen in FIG. 4, the medication is poured into the syringe cylinder 4 from the medication bottle 3. This is achieved in that there is a fluid connection 12 between the medication bottle 3 and the syringe cylinder 4, wherein a first non-return valve 13 is arranged in the fluid connection 12 which ensures that, in the case of a movement of the front end 5 of the plunger 6 from left to right in FIG. 4, the fluid connection 11 is open and thus the medication is sucked out of the medication bottle 3 into the syringe cylinder 4. In the case of the opposite movement of the plunger 6, the first non-return valve 13 is closed with the result that the medication can be dispensed via the front end 11 of the syringe 1. For this, between the front end 11 of the syringe 1 and the syringe cylinder 4 a second non-return valve 14 is arranged which, in the case of a movement of the front end 5 of the plunger 6 from right to left in FIG. 4, opens a fluid connection between the syringe cylinder 4 and the front end 11 and, in the case of an opposite movement, closes this fluid connection. An injection cannula (not shown) can be attached to the front end 11.

As can be seen in particular from the sectional representation in FIG. 4, the bottle holder 2 comprises a holding portion 15 formed substantially in the shape of a hollow cylinder which tapers towards the syringe cylinder 4 and the end 16 of which facing away from the syringe cylinder 4 is open. The holding portion 15 comprises a wall 53 and the shape of the holding portion 15 can also be referred to as basket-, shell- or pot-like and is substantially adapted to the shape of the medication bottles 3 to be held.

Figure 2:
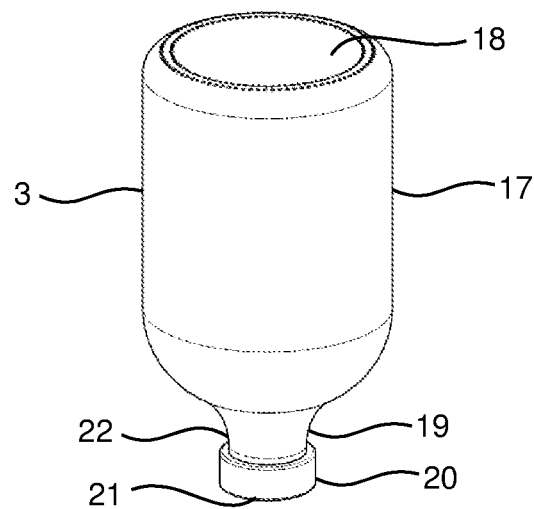
FIG. 2 is a perspective view of a bottle to be accommodated on the holder according to FIG. 1.

As is shown in FIG. 2, a medication bottle 3 usually has, for example, a cylindrical body 17 which is sealed at one end with a base 18 and, at the opposite end, tapers to a neck 19, the open end of which is sealed with a cap 20 (e.g. an aluminum cap), which has a pierceable film 21 in front of the open end of the neck 19. As is shown in FIG. 2, the external diameter of the cap 20 is larger than the external diameter of the neck 19 in this area with the result that there is an undercut 22. The bottle 3 shown in FIG. 2 has a volume of 100 ml. The external diameter of the cap 20 is 20 mm and the height of the cap 20 is 7 mm.

As can be seen in FIG. 4, the holding portion 15 is attached to a receiving section 24 of the syringe cylinder 4 with its tapered end 23 opposite the end 16. In the present embodiment, a screw connection is realized. However, any other type of connection, in particular any other type of permanent connection, is possible. In the receiving section 24, there is seated a stop 25 with a stop surface 26 and a piercing hollow spike 27 protruding beyond the stop surface.

Furthermore, the holding portion 15 comprises a guideway 28, in which three clamping elements 29, 30, 31 are mounted so as to be moveable in a direction transverse to the first direction in which the piercing hollow spike 27 extends. The clamping elements 29 to 31 (which can also be referred to as catches 29-31) lie one on another in the first direction and can be moved in the guideway 28 independently of each other. The three clamping elements 29 to 31 are formed identical such that the structure of the first clamping element 29 is described in detail in the following with reference to FIGS. 5 to 7.

The clamping element 29 comprises a clamping section 32 with a through-hole 33 and can therefore also be referred to as annular. The clamping section 32 comprises a first end 34 with a triangular marking 35 which indicates a sliding direction for the insertion of the medication bottle 3, as is described in detail below. However, the marking 35 can also be omitted.

On the second end 36 of the clamping section 32 lying opposite the first end 34, two spring arms 37, 38 are formed in a V-shaped arrangement, each of which comprises a rectilinearly extending section 39, 40, which is spaced apart from the clamping section 32. In the area of the second end 36, in each case a first stop bar 41, 42 extends from each section 39, 40 in a direction away from the clamping section 32. In addition, each spring arm 37, 38 comprises, on its free end 43, 44, a second stop bar 45, 46, which extend in each case away from the clamping section 32. The first clamping element 29 has a constant thickness with the result that, in this aspect, it can also be referred to as plate-shaped.

Figure 5:
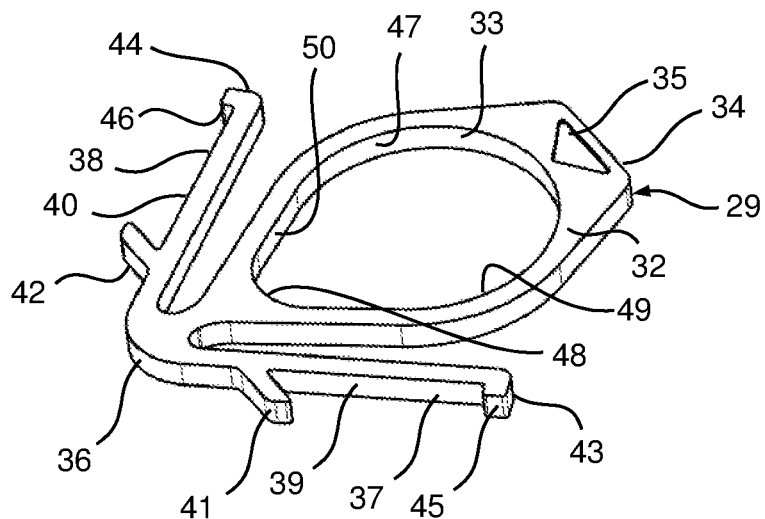
FIG. 5 is a perspective view of the first clamping element.
Figure 6:
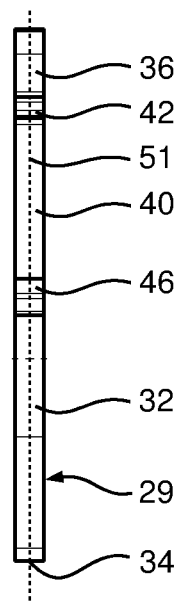
FIG. 6 is a side view of the first clamping element from FIG. 5.
Figure 7:
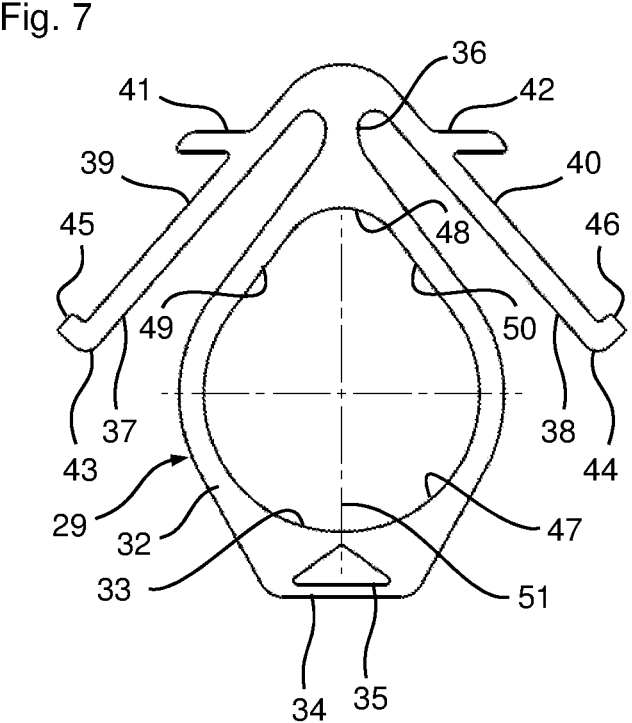
FIG. 7 is a front view of the first clamping element from FIG. 5.

As is to be seen in particular from the representations in FIGS. 5 and 7, the through-hole 33 is not formed perfectly circular but effectively has a droplet shape, an oval shape or an egg shape, which results from the fact that, at the first end 34, the through-hole 33 is bordered by a first circular path section 47 and, at the second end, is bordered by a second circular path section 48 with a smaller radius than that of the first circular path section 47, wherein the two circular path sections 47 and 48 are connected by two rectilinearly extending connecting sections 49, 50. The distance between the two connecting sections 49, 50, and thus the clear width, decreases in the direction towards the second end 36.

The first clamping element 29 is symmetrical relative to a central plane in which the central axis 51 of the first clamping element 29 runs and which is perpendicular to the plane of drawing according to FIG. 7. It can also be said that the first clamping element 29 is rotationally symmetrical through 180 relative to the central axis 51. Furthermore, the first clamping element 29 is symmetrical relative to a plane in which the central axis 51 according to the representation in FIG. 6 runs and which is perpendicular to the plane of drawing in FIG. 6. The first clamping element 29 according to FIG. 7 thus looks the same when it is rotated about the central axis 51 through 180° in the representation in FIG. 7. The marking 35 can be formed only on one side or on both sides. There can also be no marking on either side.

Figure 8:
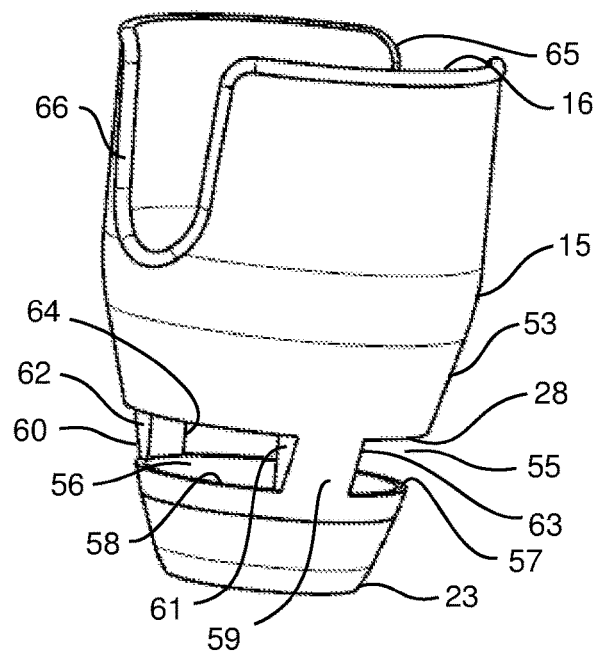
FIG. 8 is a perspective view of the holding portion.
Figure 9:
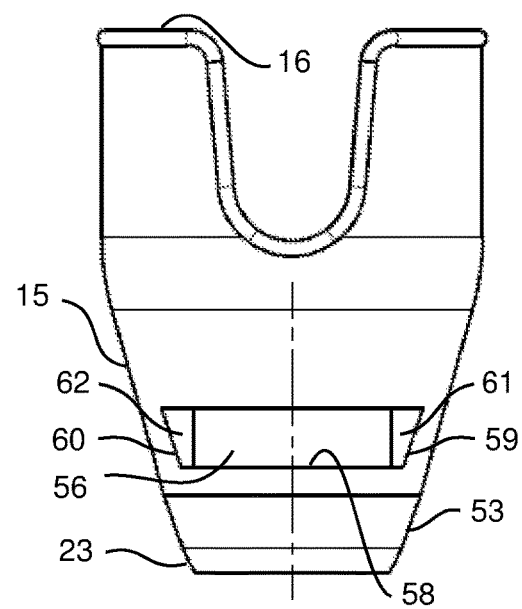
FIG. 9 is a front view of the holding portion from FIG. 8.
Figure 10:
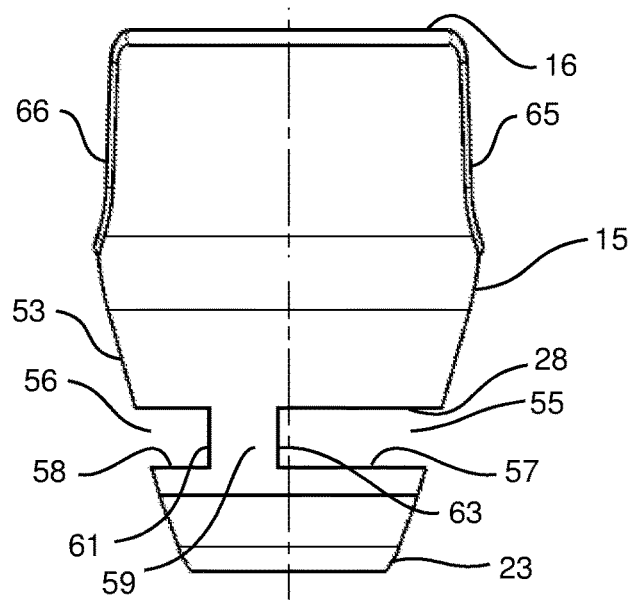
FIG. 10 is a right-hand side view of the holding portion from FIG. 8.

The guideway 28 for the clamping elements 29-31 is realized in the holding portion 15 by a first and second guideway opening 55, 56 in the wall 53, as can be seen in FIGS. 8 to 10. Through the two guideway openings 55, 56 lying opposite each other, a first and second bearing surface 57, 58 is provided in the wall 53. The two guideway openings 55 and 56 are separated by a first and second web 59 and 60, which in each case form a first stop surface 61 and 62 for the first stop bar 41 and 42 of the first clamping element 29 and a second stop surface 63, 64 for the second stop bar 45, 46 of the first clamping element 29.

When the first clamping element 29 is positioned in the guideway 28, it bears on the bearing surfaces 57 and 58 and presses the spring arms 37, 38 with their sections 39 and 40 against the webs 59 and 60 from inside, wherein, in the representations of FIGS. 8 and 10, the first stop bars 41 and 42 of the spring arms 37 and 38 protrude outwards to the left from the first or second web 59, 60, respectively, and the second stop bars 45, 46 protrude to the right from the first or second web 59, 60, respectively. Since the dimensions of the first clamping element 29 and the guideway 28 are chosen such that the webs 59 and 60 press the spring arms 37, 38 inwards towards the clamping section 32, this leads, when there is no bottle 3 inserted in the bottle holder 2, to the first clamping element 29, seen in FIG. 10, being moved towards the right until the first stop bar 41, 42 abuts against the first stop surface 61 and 62. This position of the first clamping element 29 can be referred to as clamping position.

Furthermore, it is possible, by pressing against its first end 34 (and thus by applying a force from right to left seen in FIG. 10), to slide the first clamping element 29 from right to left, in FIG. 10, until the second stop bar 45, 46 abuts against the second stop surface 63, 64. This position can be referred to as insertion position. As soon as force is no longer applied to the first clamping element 29 against the first end 34, the first clamping element 29 will move towards the right again (seen in FIG. 10) as a result of the restoring force through the spring arms 37, 38. If no bottle is inserted, the movement ends as soon as the first stop bars 41 and 42 abut against the first stop surfaces 61 and 62.

As has already been stated, the second and third clamping elements 30 and 31 are formed identical to the first clamping element 29. In the embodiment described here, the second clamping element lies in the guideway 28 on the first clamping element 29 and the third clamping element 31 lies in the guideway 28 on the second clamping element 30. The height of the two guideway openings 55 and 56 is chosen such that the three clamping elements 29 to 31 are guided securely.

If a medication bottle 3 is to be accommodated in the bottle holder 2, in the described manner, by applying a force in each case to their first end 34, the three clamping elements 29 to 31 are to be brought into the insertion position, in which the area with the first circular path section 47 of the through-hole 33 lies as concentrically as possible with the piercing hollow spike 27 with the result that the cap 20 of the medication bottle 3 can be moved through the through-holes 33 in the direction towards the stop surface 26 until the cap 20 abuts against the stop surface 26. In the process, the pierceable film 21 is pierced by the piercing hollow spike 27.

In this position of the bottle 3, no force is applied to the clamping elements 29 to 31 with the result that the three clamping elements 29 to 31 are moved back in the direction of their clamping position as a result of the restoring force of the spring arms 37 and 38. This movement ends at the bottle neck 19, however, as can be seen in particular in the sectional view of FIG. 4, since, without a bottle inserted, the clamping position for each of the clamping elements 29 to 31 lies further in the direction towards the first guideway opening 55. In other words, the first stop bars 41 and 42 of the clamping elements 29 to 31 do not yet abut against the first stop surfaces 61 and 62 with the result that there is still a certain spring tension which presses the rim of the clamping section 32 bordering the respective through-hole 33 against the bottle neck 19. As can be seen in FIG. 4, the clamping elements 29 to 31 engage directly into the undercut 22; this applies in particular to the first clamping element 29.

Because of the described droplet-shaped formation of the through-holes 33, areas of the rectilinear connecting sections 49 and 50 bear on the cap 20 from the undercut 22 with the result that, advantageously, a force is also exerted on the bottle 3 in the direction towards the stop surface 26, whereby a secure fixing of the bottle 3 in the holder 2 is guaranteed. Of course, the second clamping element 30, which lies directly on the first clamping element 29, also supplies a force in the direction onto the stop surface 26 via the first clamping element 29. This also applies to the third clamping element 31, which brings about an application of force in the direction onto the piercing surface 26 via the second and first clamping elements 30 and 29.

When the medication bottle 3 is to be removed from the holder (for example when it is empty), the three clamping elements 29 to 31 only need to be slid into their open positions by applying a force to their respective first end 34 with the result that the bottle 3 can then be removed from the top.

Through the described formation of the bottle holder 2 according to the invention, not only is the described simple and secure fixing of the medication bottle 3 achieved. It is also possible to accommodate and to fix different medication bottles 3, which differ in terms of their size and in particular the size of the diameter of the neck 19 and thus also the size of the diameter of the cap 20 and the height of the cap 20 and thus the distance of the position of the undercut 22 from the stop surface 26, securely in the holder 2 when the bottle 3 is inserted in the holder 2.

Figure 12:
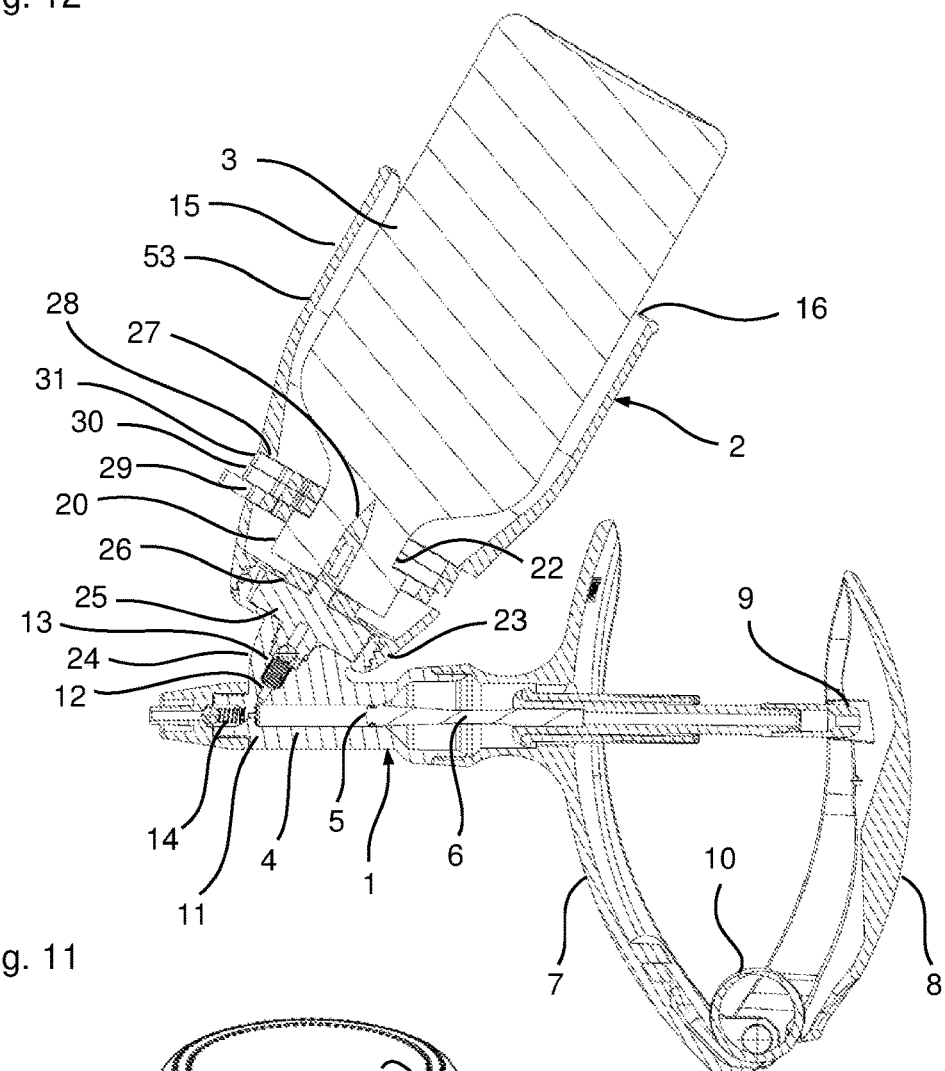
FIG. 12 is a sectional view of the syringe with the holder in the same way as in FIG. 4, wherein the bottle according to FIG. 11 is fixed in the holder.
Figure 11:
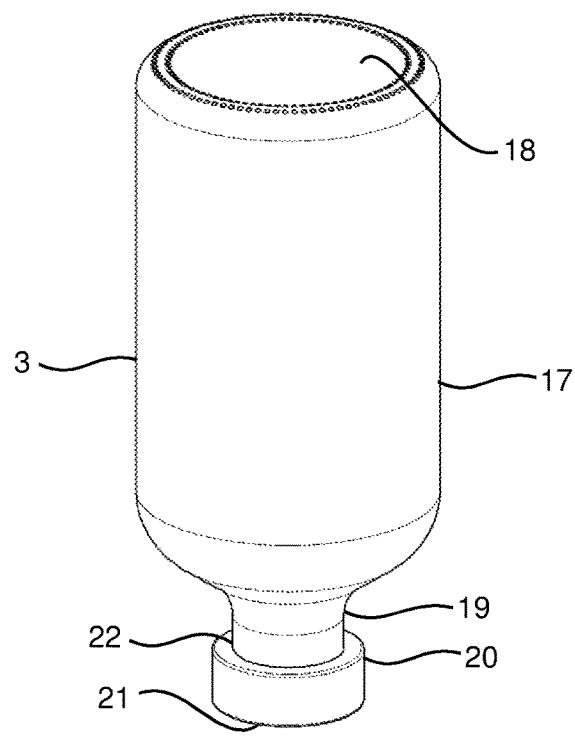
FIG. 11 is a perspective view of a further bottle.

In FIG. 11, such a larger bottle 3, which has a volume of 200 ml, is shown. A comparison with FIG. 2 clearly shows that the height of the cap 20 (10.5 mm here), the external diameter of the cap (30 mm here) and the neck diameter are larger. The bottle 3 from FIG. 11 can be inserted and fixed in the holder 2 in the manner described. In turn, the three clamping elements 29 to 31 must therefore be brought into the insertion position by the application of a force. Then, the bottle 3 is inserted into the holder 2 with the cap 20 first and pressed onto the stop surface 26, whereby the piercing hollow spike 27 is stabbed through the pierceable film 21. In this state, the application of force to the three clamping elements 29 to 31 is ended with the result that the three clamping elements 29 to 31 are moved back into their clamping position as a result of the spring force of the spring arms 37 and 38. As is shown in FIG. 12, the first clamping element 29 abuts against the side of the cap 20. The second clamping element 30 abuts against the neck 19 in the area of the undercut 22 and the third clamping element 31 also abuts against the neck 19. The second and third clamping elements 30 and 31 thus bring about an application of force in the direction towards the receiving surface 26, which in turn brings about a secure fixing of the bottle 3 in the holder 2.

Furthermore, a further medication bottle 3 (not shown), which has a volume e.g. of 250 ml, can also be fixed on the bottle holder 2 according to the invention. In the case of such a medication bottle, the external diameter of the cap 20 can be 33 mm and the height of the cap can be 14 mm. In the inserted state, the first and second clamping elements 29 and 30 then abut against the cap 20 and the third clamping element 31 engages in the undercut 22.

Since the holder 2 according to the invention in the embodiment described here is designed for cap heights of 7, 10.5 or 14 mm, the thickness of the individual clamping elements 29-31 is preferably 3.5 mm. It can lie in the range of e.g. 3 to 10 mm, 3 to 5 mm or 3.5 to 4.5 mm.

The radii of curvature of the circular paths 47 and 48 can preferably be adapted to the dimensions of the different medication bottles 3 to be accommodated and thus to a set of bottles 3. The radius of curvature of the first circular path section 47 is preferably larger than the corresponding radius of the cap 20 with the largest external diameter of the set of bottles. The radius of curvature of the second circular path section 48 is preferably smaller than the corresponding radius of the bottle neck with the smallest external diameter of the set of bottles. It is thus ensured that each of the medication bottles of the set of bottles can be moved through the through-holes 33 when the clamping elements are in the insertion position. The choice of the radius of the second circular path section 48 ensures that portions of the two linear sections 49 and 50 always engage on the rear side of the cap 20 or in the undercut 22 with the result that a force is exerted in the direction towards the stop surface 26 on the cap 20 on two contact points or contact areas.

In the embodiment example described here, three clamping elements 29-31 stacked one on top of the other are provided. Of course, the holder according to the invention can also have only one or two clamping elements or four, five or more clamping elements. In addition, it is possible for the clamping elements to have different thicknesses. The thicknesses of the clamping elements can be adapted to the differences in the heights of the various bottles of the bottle set to be accommodated, for which the bottle holder 2 is designed.

The holding portion 15 can be produced in particular from plastic. The plastic can be transparent. As can be seen in particular in FIGS. 8 and 9, the holding portion 15 can have two openings 65, 66 lying opposite each other, which extend from the end 16 to the tapered end 23 of the holding portion 15. The length of the extension can be in the range from 0.5 to 0.25 of the total length (or height) of the holding portion 15. The openings 65 and 66 serve in particular to make it easier to remove a medication bottle 3 that is relatively short from the holding portion 15.

The clamping elements 29-31 are preferably produced from plastic.

With the bottle holder 2 according to the invention, which can also be referred to as a universal basket, bottles 3 with different dimensions can thus be held and fixed without problems.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A bottle holder for a syringe, comprising:
   a stop surface;
   a piercing hollow spike protruding beyond the stop surface and extending in a first direction;
   a guideway;
   a first clamping element; and
   a second clamping element,
   wherein each of the first and second clamping elements are arranged one on another along the first direction and are mounted in the guideway so as to be moveable along a second direction transverse to the first direction,
   wherein each of the first and second clamping elements include a through-hole and each of the first and second clamping elements are moveable back and forth between an insertion position and a clamping position,
   wherein, when the first and second clamping elements are in the insertion position, a neck of the bottle is movable through the through-holes until the front end of the bottle abuts against the stop surface such that the piercing hollow spike pierces a film at the front end of the bottle, and
   wherein at least one of the first and second clamping elements, when in the clamping position, presses against the neck of the bottle, which abuts with a front end against the stop surface, the bottle is clamped in the holder.

2. The bottle holder according to claim 1, wherein at least one of the first and second clamping elements, when in the clamping position, abuts against an undercut on the neck of the bottle.

3. The bottle holder according to claim 1, wherein each of the first and second clamping elements includes at least one spring arm which applies a force in the direction towards the clamping position to the clamping element mounted in the guideway.

4. The bottle holder according to claim 3, wherein each of the first and second clamping elements comprises two spring arms which are arranged in a V shape.

5. The bottle holder according to claim 3, wherein at least one spring arm of each of the first and second clamping elements comprises a first and a second stop bar, which extend away from the through-hole, wherein the first and second stop bars define end positions of the movement of the clamping element in the second direction.

6. The bottle holder according to claim 1, wherein at least one of the first and second clamping elements is formed in one piece.

7. The bottle holder according to claim 1, further comprising a shell-shaped holding portion with a wall, wherein the guideway comprises two guideway openings lying opposite each other in the wall.

8. The bottle holder according to claim 1, wherein the rim of the through-hole of one of the first and second clamping elements, seen in the first direction onto the clamping element, comprises two rounded ends of different sizes lying opposite each other along the second direction, which are connected by two connecting sections.

9. The bottle holder according to claim 8, wherein at least one of the rounded ends is formed as a circular path section.

10. The bottle holder according to claim 1, wherein at least one of the first and second clamping elements comprises an annular clamping section with the through-hole.

11. The bottle holder according to claim 1, wherein at least one of the first and second clamping elements is rotationally symmetrical through 180° about an axis along the second direction.

12. The bottle holder according to claim 1, wherein at least one of the first and second clamping elements has a constant thickness along the first direction.

13. The bottle holder according to claim 1, wherein the first and second clamping elements lie directly one on another.

14. The bottle holder according to claim 1, wherein the first and second clamping elements are formed identical.

15. A syringe in combination with a bottle holder according to claim 1.

* * * * *